(12) United States Patent
Horton et al.

(10) Patent No.: US 12,158,465 B2
(45) Date of Patent: Dec. 3, 2024

(54) DEVICE AND METHOD FOR SAMPLE ISOLATION

(71) Applicant: GLOBAL LIFE SCIENCES SOLUTIONS OPERATIONS UK LTD, Sheffield (GB)

(72) Inventors: Jeffrey Kenneth Horton, Cardiff (GB); Peter James Tatnell, Cardiff (GB); Alan Pierce, Cardiff (GB); Alexander Schenk, Dassel (DE); Rebecca Ngaire Fullerton, Bulwark (GB)

(73) Assignee: GLOBAL LIFE SCIENCES SOLUTIONS OPERATIONS UK LTD, Sheffield (GB)

( * ) Notice: Subject to any disclaimer, the term of this patent is extended or adjusted under 35 U.S.C. 154(b) by 1005 days.

(21) Appl. No.: 16/607,233

(22) PCT Filed: Apr. 11, 2018

(86) PCT No.: PCT/EP2018/059327
§ 371 (c)(1),
(2) Date: Oct. 22, 2019

(87) PCT Pub. No.: WO2018/197218
PCT Pub. Date: Nov. 1, 2018

(65) Prior Publication Data
US 2020/0378958 A1 Dec. 3, 2020

(30) Foreign Application Priority Data

Apr. 27, 2017 (GB) ...................................... 1706680

(51) Int. Cl.
| | |
|---|---|
| *C07K 1/34* | (2006.01) |
| *B01D 69/14* | (2006.01) |
| *C07K 1/36* | (2006.01) |
| *G01N 33/538* | (2006.01) |
| *G01N 33/543* | (2006.01) |

(52) U.S. Cl.
CPC ......... *G01N 33/538* (2013.01); *B01D 69/144* (2013.01); *C07K 1/34* (2013.01); *C07K 1/36* (2013.01); *G01N 33/54393* (2013.01)

(58) Field of Classification Search
None
See application file for complete search history.

(56) References Cited

U.S. PATENT DOCUMENTS

| 2009/0143570 A1 | 6/2009 | Jiang et al. |
| 2012/0164750 A1 | 6/2012 | Gjerde et al. |

FOREIGN PATENT DOCUMENTS

| GB | 2538955 A | 12/2016 |
|---|---|---|
| WO | 91/10492 A1 | 7/1991 |
| WO | 02/16580 A2 | 2/2002 |
| WO | 2005/012521 A1 | 2/2005 |
| WO | 2005/037988 A2 | 4/2005 |
| WO | 2010/014970 A1 | 2/2010 |
| WO | 2010/140598 A1 | 12/2010 |
| WO | 2012/113911 A1 | 8/2012 |
| WO | 2013/062476 A1 | 5/2013 |
| WO | 2013/083260 A1 | 6/2013 |
| WO | 2014/072354 A1 | 5/2014 |
| WO | 2015/126523 A1 | 8/2015 |
| WO | 2016/007755 A1 | 1/2016 |
| WO | 2017/014817 A1 | 1/2017 |

OTHER PUBLICATIONS

PCT International Search Report and Written Opinion for PCT Application No. PCT/EP2018/059327 mailed May 18, 2018 (14 pages).
Great Britain Search Report for GB Application No. 1706680.4 mailed Feb. 1, 2018 (4 pages).
Tolosa et al., "Column-Based Method to Simultaneously Extract DNA, RNA, and Proteins from the Same Sample," Biotechniques, 2007, 43(6):799-804.

*Primary Examiner* — Benjamin P Blumel
(74) *Attorney, Agent, or Firm* — Eversheds-Sutherland (US) LLP

(57) ABSTRACT

The present invention relates to a device and method for sample preparation and collection. More closely the invention relates to a device to isolate DNA, RNA and proteins or other biomolecules in one single step from the same undivided sample.

10 Claims, 1 Drawing Sheet

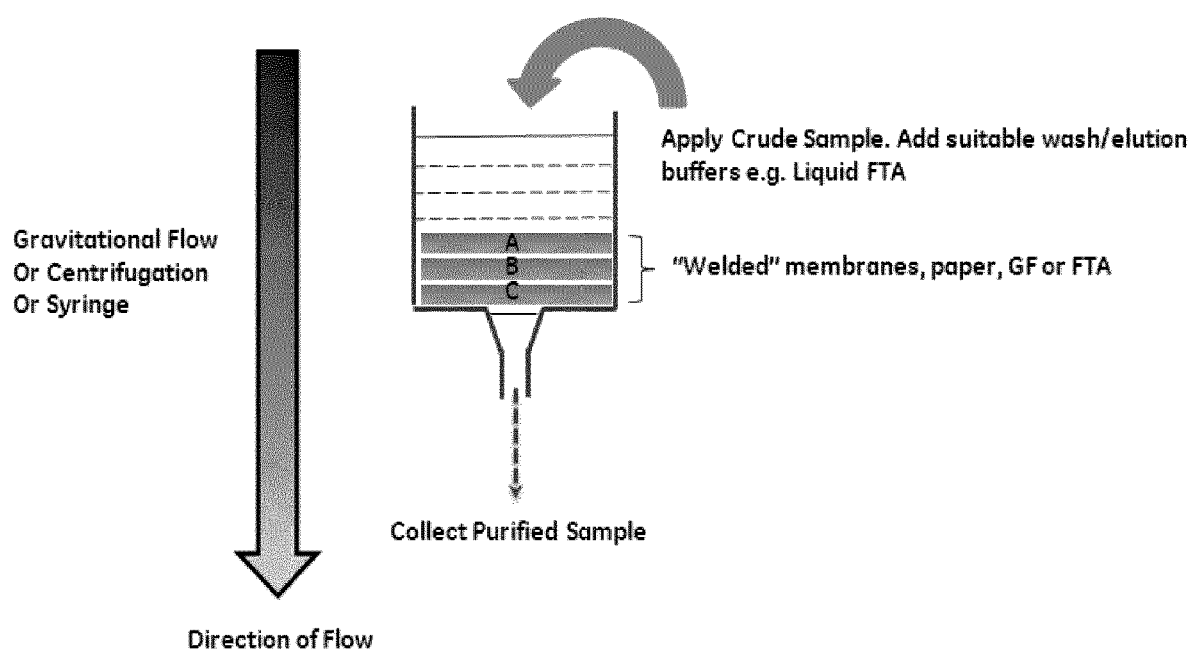

DEVICE AND METHOD FOR SAMPLE ISOLATION

CROSS REFERENCE TO RELATED APPLICATIONS

This application claims the priority benefit of PCT/EP2018/059327 filed on Apr. 11, 2018, which claims priority benefit of Great Britain Patent Application No. 1706680.4 filed on Apr. 27, 2017, the entire contents of which are hereby incorporated by reference herein.

FIELD OF THE INVENTION

The present invention relates to a device for sample preparation and collection. More closely the invention relates to a device to isolate DNA, RNA and proteins or other biomolecules in one single step from the same undivided sample.

BACKGROUND OF THE INVENTION

Until recently, researchers in fields such as molecular genetics typically use three or more separate methods or kits to isolate DNA, RNA and proteins or other biomolecules in a sample for use in downstream applications. However, the use of a divided sample could potentially alter results and interpretation due to heterogeneity between different aliquots of cell, blood or tissue sample. The demand for reasonable correlations and relationships between transcript expression, protein and copy number variation and single nucleotide polymorphism (SNP) detection has resulted in the demand for the development of methods for isolating genomic DNA, total RNA and total protein from the same, undivided sample which has resulted in the availability of a small number of commercially available kits.

Frequently in chemical, biological or materials procedures it is necessary to isolate, purify and store desired substances from complex mixtures such as biological fluids. Column chromatography of various types is commonly used for such procedures. In particular, spin-column chromatography is frequently employed to enrich for analytes. Such spin-columns are usually of a simple design and usually contain a single separation media such as cross-linked dextrans (e.g. Sephadex), polacrylamides ion-exchange resins, glass fibre or silica gels of various types. Usually three or more separate columns are employed to isolate DNA, RNA and proteins or other biomolecules from a single sample for use in downstream applications. However, there is a great need to simplify the isolation, separation and storage of biomolecules, whereby more than one analyte can be prepared from a single, undivided sample. Furthermore, the efficient recovery and storage of labile biomolecules (such as RNA & protein) requires rapid, reliable separation processes under mild conditions.

Thus, there is still the need of a particular device where DNA, RNA and protein are prepared from the same sample to prepare nucleic acids and/or biomolecules, and, to correlate DNA, RNA and protein data directly. This would ensure that data were not an artefact of experimental design, but were characteristic of the sample.

SUMMARY OF THE INVENTION

The present invention describes a modular and flexible approach to separate and store biomolecules using fixed or interchangeable papers. It describes a device that will contain cellulose papers, glass fibre, specialised adsorptive or affinity membranes such as nitrocellulose, FTA or FTA-elute-like supports for the chromatographic isolation (and storage) of proteins, peptides and/or nucleic acids from a single sample. The adsorptive matrix may be functionalised as required.

The efficient recovery and storage of labile biomolecules requires rapid, reliable separation processes using mild conditions. Adsorptive membranes and papers are currently available with a range of functionalised chemistries and geometries which permit their application as clarification, concentration, fractionation and a bio-recovery sequence or workflow.

The present invention describes a system which is readily adaptable for the rapid separation and/or storage of biomolecules from an eluent or tissue sample.

In a first aspect the invention relates to a device for simultaneous protein and nucleic acid separation comprising a column with an inlet and an outlet, wherein the column is provided with at least two, preferably three (A, B, C), types of membranes stacked on top of each other inside the column, wherein the device comprises an upper membrane A which is a sieving membrane, a lower membrane B which is a silica, glass fibre or quartz fibre membrane for nucleic acid separation, and/or a lower membrane C which is a ligand provided membrane for protein separation.

The order in which membranes B and C are arranged in the column may be reversed. Preferably one or more, such as 1-10, of each the membranes A, B and/or C are provided, more preferably one of each kind of the membranes A, B and C is provided in the device.

The sieving membrane A preferably excludes particles larger than a 0.10 μm, such as larger than 0.22 μm or 0.45 μm.

The protein separating membrane C is preferably provided with an affinity ligand, ion exchange ligand or hydrophobic interaction ligand.

The device according to the invention may be based on a pipette tip, a card with stacked membranes, a microtiter plate, a syringe, a centrifuge tube or a micro-spin column.

In a second aspect, the invention relates to a method for simultaneous protein and nucleic acid separation comprising adding a sample to the above described device, and eluting proteins and nucleic acids separately.

The device according to the invention is thus provided with layers of different function and the terms of the different layers, such as membranes, matrices, solid supports, filters, papers, are used interchangeable throughout the description and claims.

BRIEF DESCRIPTION OF THE DRAWING

FIG. 1 is a schematic view of a membrane-stacked device of the invention comprising several solid matrices exhibiting different properties.

DETAILED DESCRIPTION OF THE INVENTION

The invention describes the separation and purification device for multiple biomolecules from a single sample, using membranes, for example, silica, glass fibre or paper, nitrocellulose chemically cross-linked with suitable ligands to isolate and store the target biomolecules. Thus this invention is not limited in scope to particular membranes, matrices or supports, but may be used with any matrix well known in the art. Examples of affinity systems may involve the use of antibodies, GST, HisTag, charged membranes or paper (e.g. ion exchangers, or polar groups) immobilised enzymes and similar. For example, sequestering agents may be chemically functionalised to a suitable support to remove interfering agents. Different types of ligands may be covalently attached to for example cellulose membranes which would then act as affinity ligands. Activation and derivatisation may be through (i) epoxy activation (ii) glutaraldehyde (iii) diazotisation. Linkage of ligands to glass fibre may be via esterification, and organic silanes. Cross linking may also be performed through the use of glutaraledhyde, bis[3-(trimethoxyysilyl)-propyl]amine, 1,2-bis(triethoxylsilyl)-ethane, or 1,3-diethoxy-1,1,3,3-tetramethyldisiloxane.

The device of the invention allows isolation of native protein, RNA and DNA from a single sample applied to a device containing the appropriate paper or membrane types. The format is not a limitation and could be based upon i) a card using a membrane stack, ii) a pipette tip device iii) a micro-titre plate or iv) a micro spin column, or (v) a membrane stack device (see FIG. 1).

Base/uncoated filter papers, e.g. Whatman 903, can be impregnated with i) a mild non-ionic detergent such as NP40, Triton X-100, CHAPS etc., to allow for cell lysis without the subsequent denaturation of proteins and/or:

ii) chemicals such as polyvinyl alcohol (PVA), polyethyloxazoline (PEOX), poly(vinylpyrrolidone)(PVP) and poly(ethyleimine) (PEI), polyethylene glycol (PEG) etc., that minimise/prevent the absorption of proteins thereby facilitating their elution. The above chemicals have been described in GB 1103256.2, GB 1103257.0 and GB 1103258.8.

Thus, the device is not limited for the isolation of nucleic acids. Numerous affinity ligands may be immobilised onto the membranes or solid supports and these may be used to purify any proteins, such as lectins, enzymes, natural protease inhibitors, globulin, fibronectin etc. from natural and complex mixtures.

EXAMPLE

For this example reference is made to FIG. 1.

A funnel shaped device in the form of a syringe or column provided with membranes is shown in FIG. 1. Alternatively, the membrane-stacked device could for example be in a micro-spin column format. The device is provided with membranes or matrices A, B and C. One or more of respective membrane/matrix is provided.

In this example membrane A is a 0.45 or 0.22 μm filter to remove particulate materials from a crude sample, matrix B is a silica membrane, glass fibre membrane or quartz fibre membrane for nucleic acid isolation and storage, and membrane C a nitrocellulose membrane cross-linked with a suitable ligand to generate an affinity matrix or a matrix derivatised with an ion exchanger or polar substance to separate on the basis of charge and/hydrophobicity. The order of the membranes/matrices B-C is interchangeable to achieve the desired separation.

A sample, for example a biological sample such as serum, is applied on top or at the inlet of the device and the device is washed with suitable buffers. The flow is through the top inlet through the layers A-C and out of the device through the bottom outlet. Coarse material stays on top of membrane A, while nucleic acids are isolated on membrane B and proteins on membrane C. Nucleic acids and proteins are eluted separately from the device with suitable buffers.

As stated above the membranes B-C are interchangeable. The efficiency of DNA, RNA and protein recoveries using any of the methods described above and for the combinations A, B, C and A, C, B is determined by i) nucleic acid detection—quantity and purity is assessed by spectrophotometry, qPCR, RT qPCR etc. ii) protein quality is analysed by techniques such as ELISA, PAGE, and for native protein-functional enzymatic activity.

The invention claimed is:

1. A device for simultaneous protein and nucleic acid separation comprising a column with an inlet and an outlet, wherein the column is provided with at least three types of membranes directly stacked on top of each other inside the column, wherein the device comprises an upper membrane A which is a sieving membrane configured to collect course materials, a middle membrane B which is a silica, glass fibre or quartz fibre membrane for nucleic acid separation, and a lower membrane C which is a ligand provided membrane for protein separation.

2. The device according to claim 1, wherein the order in which membranes B and C are arranged in the column may be reversed.

3. The device according to claim 1, wherein one or more of each type of the membranes A, B and C are provided.

4. The device according to claim 1, wherein one of each kind of the membranes A, B and C is provided.

5. The device according to claim 1, wherein the sieving membrane A excludes particles larger than 0.10 μm.

6. The device according to claim 1, wherein the protein separating membrane C is provided with an affinity ligand, ion exchange ligand or hydrophobic interaction ligand.

7. A method for simultaneous protein and nucleic acid separation, comprising adding a sample to the device according to claim 1 and eluting proteins and nucleic acids separately.

8. The device according to claim 3, wherein 1-10 of each of the membranes A, B and C are provided.

9. The device according to claim 5, wherein the sieving membrane A excludes particles larger than 0.22 μm.

10. The device according to claim 5, wherein the sieving membrane A excludes particles larger than 0.45 μm.

* * * * *